(12) United States Patent
Catt et al.

(10) Patent No.: US 6,951,631 B1
(45) Date of Patent: *Oct. 4, 2005

(54) TEST KITS AND DEVICES

(75) Inventors: Michael Catt, Northampton (GB); Peter Lenko, Kappel (AT); Michael T. Pearson, Kingston Upon Thames (GB)

(73) Assignee: Inverness Medical Switzerland GmbH, Zug (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/935,717

(22) Filed: Sep. 23, 1997

(30) Foreign Application Priority Data

Sep. 27, 1996 (EP) .............................................. 96307089

(51) Int. Cl.[7] ........................ G01N 21/86; G01N 33/76; G01N 33/74

(52) U.S. Cl. ............................ 422/56; 422/58; 422/61; 422/68.1; 422/82.05; 422/82.09; 422/82.02; 435/7.9; 435/7.93; 436/514; 436/65; 436/169

(58) Field of Search ............................. 422/58, 56, 61, 422/82.05, 82.09, 82.02, 68.1; 436/514, 65, 165, 169, 35, 518; 435/7.91, 7.93, 7.94, 7.9, 7.1; 600/551; 356/446

(56) References Cited

U.S. PATENT DOCUMENTS 3,141,740 A    7/1964  Wild 3,406,015 A   10/1968  Foster (Continued)

FOREIGN PATENT DOCUMENTS

| CA | 1 048 001 | 2/1979 |
|----|-----------|--------|
| CA | 1 183 080 | 2/1985 |

(Continued)

OTHER PUBLICATIONS

Adlercreutz et al., "Prediction of ovulation by urinary estrogen assays", J. Steroid Biochem, 1980, v. 12, pp 395–348.

(Continued)

*Primary Examiner*—L. F. Smith
*Assistant Examiner*—Ginny Allen Portner
(74) *Attorney, Agent, or Firm*—Oppedahl & Larson LLP

(57) ABSTRACT

A test kit for determining qualitatively or quantitatively the presence of one or more analytes in a fluid sample, comprising an assay device together with a reading device which engages with the assay device and wherein precisely located engagement of the assay device with the reading device is essential for accurate reading of the assay result, wherein precisely located engagement of the assay device with the reading device causes a 'lock-and-key' interaction, ie. a unique 3-dimensional interaction, between the assay device and reading initiation means of the reading device. Preferably the reading initiation means includes switch actuating means comprising at least one fixed projecting portion and at least one displaceable projecting portion, and a contact portion of the assay device casing comprises a recess shaped to accommodate the fixed projecting portion of the switch actuating means but not the displaceable projecting portion thereof, the contact portion also comprising an interface portion that contacts and displaces the displaceable portion of the switch actuating means when the fixed projecting portion is accommodated within the recess.

8 Claims, 6 Drawing Sheets

U.S. PATENT DOCUMENTS

| | | | |
|---|---|---|---|
| 3,406,016 A | 10/1968 | Foster et al. | |
| 3,434,801 A | 3/1969 | Scherr | |
| 3,436,186 A | 4/1969 | Mcsweeney et al. | |
| 3,749,089 A | 7/1973 | Derr | |
| 3,875,013 A | 4/1975 | Manautou et al. | |
| 3,924,609 A | 12/1975 | Friedenberg et al. | |
| 3,926,037 A | 12/1975 | Kopito et al. | |
| 3,968,011 A | 7/1976 | Manautou et al. | |
| 3,986,494 A | 10/1976 | Preti et al. | |
| 3,991,174 A | 11/1976 | Grundman | |
| 4,002,056 A | 1/1977 | Kopito et al. | |
| 4,010,738 A | 3/1977 | Preti et al. | |
| 4,013,066 A | 3/1977 | Schuster | |
| 4,031,365 A | 6/1977 | Raggiotti et al. | |
| 4,036,212 A | 7/1977 | Karuhn | |
| 4,059,986 A | 11/1977 | Schuster | |
| 4,072,045 A | 2/1978 | Kopito | |
| 4,119,089 A | 10/1978 | Preti et al. | |
| 4,123,510 A | 10/1978 | Banik et al. | |
| 4,148,304 A | 4/1979 | Mull | |
| 4,151,831 A | 5/1979 | Lester | |
| 4,151,833 A | 5/1979 | Polishuk | |
| 4,208,187 A | 6/1980 | Givner | |
| 4,232,215 A | 11/1980 | Hanley | |
| 4,246,907 A | 1/1981 | Bullock | |
| 4,261,371 A | 4/1981 | Reading, III | |
| 4,312,360 A | 1/1982 | Conway et al. | |
| 4,367,527 A | 1/1983 | Desjacques | |
| 4,370,727 A | 1/1983 | Bellet | |
| 4,377,171 A | 3/1983 | Wada | |
| 4,381,121 A | 4/1983 | Hanley | |
| 4,385,125 A | 5/1983 | Preti et al. | |
| 4,396,020 A | 8/1983 | Wolff et al. | |
| 4,408,905 A | 10/1983 | Ehrenkranz | |
| 4,443,851 A | 4/1984 | Lin | |
| 4,450,239 A | 5/1984 | Chatterton | |
| 4,465,077 A | 8/1984 | Schneider | |
| 4,466,445 A | 8/1984 | Abrams | |
| 4,475,158 A | 10/1984 | Elias | |
| 4,488,560 A | 12/1984 | Takamura | |
| 4,498,481 A | 2/1985 | Lemke | |
| 4,530,366 A | 7/1985 | Nessi et al. | |
| 4,534,362 A | 8/1985 | Schumacher et al. | |
| 4,557,273 A | 12/1985 | Stoller et al. | |
| 4,614,715 A | 9/1986 | Tsibris et al. | |
| 4,670,401 A | 6/1987 | Cutler et al. | |
| 4,676,254 A | 6/1987 | Frohn | |
| 4,685,471 A | 8/1987 | Regas et al. | |
| 4,691,714 A | 9/1987 | Wong et al. | |
| 4,752,880 A | 6/1988 | Aeschlimann | |
| 4,753,247 A | 6/1988 | Kirsner | |
| 4,770,186 A | 9/1988 | Regas et al. | |
| 4,779,627 A | 10/1988 | Kosasky | |
| 4,921,808 A | 5/1990 | Schneyer et al. | |
| 5,043,888 A | 8/1991 | Uriarte | |
| 5,050,612 A | 9/1991 | Matsumura | |
| 5,059,394 A * | 10/1991 | Phillips et al. | 422/68.1 |
| 5,063,930 A | 11/1991 | Nucci | |
| 5,091,170 A | 2/1992 | Navot | |
| 5,108,889 A * | 4/1992 | Smith | 435/4 |
| 5,137,028 A | 8/1992 | Nishimura | |
| 5,209,238 A | 5/1993 | Sundhar | |
| 5,216,599 A | 6/1993 | Uebe et al. | |
| 5,248,593 A | 9/1993 | Hubner-Parajsz et al. | |
| 5,354,692 A * | 10/1994 | Yang et al. | 436/514 |
| 5,356,782 A * | 10/1994 | Moorman et al. | 435/7.9 |
| 5,411,858 A * | 5/1995 | McGeehan et al. | 435/4 |
| 5,445,967 A * | 8/1995 | Deuter | 436/164 |
| 5,467,778 A * | 11/1995 | Catt et al. | 600/551 |
| 5,504,013 A * | 4/1996 | Senior | 436/165 |
| 5,526,120 A * | 6/1996 | Jina et al. | 356/446 |
| 5,602,040 A * | 2/1997 | May et al. | 436/514 |
| 5,611,995 A * | 3/1997 | de Zoeten et al. | 422/58 |
| D379,662 S * | 6/1997 | Pearson et al. | D24/223 |
| D379,663 S * | 6/1997 | Pearson et al. | D24/223 |
| D380,837 S * | 7/1997 | Pearson et al. | D24/223 |
| 5,656,503 A * | 8/1997 | May et al. | 436/514 |
| 5,726,010 A * | 3/1998 | Clark | 435/5 |
| 5,869,972 A * | 2/1999 | Birch et al. | 324/439 |
| 6,234,974 B1 * | 5/2001 | Catt et al. | 600/551 |
| 6,235,241 B1 * | 5/2001 | Catt et al. | 422/56 |
| 6,403,380 B1 * | 6/2002 | Catt et al. | 436/65 |
| 6,451,619 B1 * | 9/2002 | Catt et al. | 436/514 |
| 6,454,726 B1 * | 9/2002 | Catt et al. | 600/551 |
| 2002/0137220 A1 * | 9/2002 | Catt et al. | 436/65 |
| 2003/0044317 A1 * | 3/2003 | Catt et al. | 422/58 |

FOREIGN PATENT DOCUMENTS

| | | | |
|---|---|---|---|
| DE | 1 214 438 | 4/1966 | |
| DE | 28 03 152 | 7/1979 | |
| DE | 28 47 397 | 5/1980 | |
| DE | 3 037 977 | 5/1982 | |
| DE | 3 221 999 | 4/1983 | |
| DE | 3 247 750 | 6/1984 | |
| DE | 3 314 442 | 11/1984 | |
| DE | 3 325 598 | 1/1985 | |
| DE | 3 342 251 | 5/1985 | |
| DE | 3 343 020 | 6/1985 | |
| DE | 3 528 964 | 2/1987 | |
| DE | 3 609 956 | 10/1987 | |
| DE | 3 802 479 | 8/1989 | |
| EP | 0 097 851 | 6/1983 | |
| EP | 0 132 199 | 7/1984 | |
| EP | 0 011 594 | 12/1984 | |
| EP | 0 195 207 | 1/1986 | |
| EP | 0 225 054 | 10/1986 | |
| EP | 0 286 743 | 4/1987 | |
| EP | 0 339 092 | 12/1987 | |
| EP | 0 291 194 | 4/1988 | |
| EP | 0 367 615 | 11/1989 | |
| EP | 0 177 994 | 1/1990 | |
| EP | 0 383 619 | 2/1990 | |
| EP | 0 385 621 | 2/1990 | |
| EP | 0 424 102 | 10/1990 | |
| EP | 0 470 507 | 8/1991 | |
| EP | 0 476 703 | 9/1991 | |
| EP | 0 498 303 | 1/1992 | |
| EP | 0 653 625 | 11/1994 | |
| EP | 0653625 A1 * | 11/1994 | G01N/21/86 |
| EP | 0653639 | * 5/1995 | |
| EP | 0703454 A1 * | 9/1995 | G01N/21/86 |
| EP | 0703454 | * 3/1996 | |
| FR | 2 290 876 | 6/1976 | |
| FR | 2 652 092 | 3/1991 | |
| GB | 945670 | 1/1964 | |
| GB | 1 203 619 | 8/1970 | |
| GB | 2 045 480 | 10/1980 | |
| GB | 2 106 646 | 4/1983 | |
| GB | 2 116 318 | 9/1983 | |
| GB | 2 186 977 | 8/1987 | |
| WO | WO 80/02800 | 12/1980 | |
| WO | WO 84/03381 | 8/1984 | |
| WO | WO 87/02774 | 5/1987 | |
| WO | WO 90/11521 | 10/1990 | |
| WO | WO 91/15594 | 10/1991 | |
| WO | WO 94/02850 | 2/1994 | |
| WO | WO 94/04926 | 3/1994 | |
| WO | 9513531 | * 5/1995 | |
| WO | 95/13531 | * 5/1995 | G01N/21/86 |
| WO | WO 95/16920 | 6/1995 | |

OTHER PUBLICATIONS

Adlercreutz et al., "The measurement of urinary sterioid glucuronides as indices of the fertile period in women", J. Steroid Biochem, 1982, v. 17, pp 695,702.

Albertson et al., "Review Article: The prediction of ovulation and monitoring of the fertile period", Adv. Contracept, v. 3, pp 263–290.

Baird et al., "Using the ratio of urinary oestrogena nd progesterone metabolites to estimate day of ovulation", Statistics in Medicine, 1991, 10, pp 255–266.

Barnard et al., "A nonseparation, time–resolved fluoroimmunoassay to minitor ovarian function and predict potential fertility in women", Fertility and Sterility, 1989, 52(1), pp 60–65.

Bieglmayer et al., "Evaluation of a simple and fast self–test for urine luteinizing hormone", Fertility and Sterility, 1990, 53(5), pp 842–846.

Bischof et al., "Comparison of a rapid, quantitative and automated assay for urinary luteinizing hormone (LH), with an LH detection test, for the prediction of ovulation", Human Reproduction, 1991, 6(4), pp 515–518.

Bonnar, "Biological methods of identifying the fertile period", Fertility and Sterility, 1984, Eds. Harrison et al., MTP Press, pp 77–92.

Brown et al., "Appendix 1: Correlations between the mucus symptoms and the hormone markers of fertility throughout reproductive life", The Ovulation Method, 7$^{th}$ Ed., Ed. Bilings, Advocate Press, Melbourne, 1983, pp 99–125.

Brown et al., "Natural Family Planning", Am. J. Obstet. Gynecol, 1987, 157(4), Part 2, pp 1082–1089.

Brown et al., "Chemical and homogeneous immunoassay methods for the measurement of estrogens and pregnanediol and their glucuronides in urine", Non–Radiometric Assays: Technology and Application in Polypeptide and Steroid Hormone Detection, Publ. Alan R. Liss Inc., 1988, pp 119–138.

Brown et al., "New assays for identifying the fertile period",, Int. J. Gynecol Obsted, Suppl. 1, 1989, pp 111–122.

Burger, "The physiologica basis of the fertile period", Fertility and Sterility, Eds. Harrison et al., MTP Press, 1984, pp. 51–58.

Burger, Estradiol: the physiological basis of the fertile period:, Int. J. Gynecol Obstet, Suppl 1, 1989, pp 5–9.

Campbell, "Methods of monitoring ovarian function and predicting ovulation: summary of a meeting", Research Frontiers in Fertility Regulation, 1985, 3(5), pp 1–16.

Cardone et al., "Objective and subjective data for fertile period diagnosis in women: comparison of methods", Clin Exp Obst Gyn, XIX, 1992, 1, pp 15–24.

Cekan et al., "The prediction and/or detection of ovulation by means of urinary steroid assays", Contraception, 1986, 33(4), pp 327–345.

Collins et al., "The concentrations of urinary oestrone–3–glucuronide, LH and pregnanediol–3a–gluronide as indices of ovarian function", Acta Endocrinologica, 1979, 90, pp 336–347.

Collins et al., "Biochemical indices of the fertile period in women", Int J Fertil, 1981, 26(3), pp 196–202.

Collins et al., "Ovulation prediction and detection by the measurement of steroid glucuronides", Proc X Int Congress on Fertility and Sterility, 1981, pp 19–33.

Collines et al., "Biochemical methods for predicting ovulation", Fertility and Sterility, 1984, pp 59–69.

Collins, "Hormonal indices of ovulation and the fertile period", Adv Contracept, 1985, 1, pp 279–294.

Collines, "Biochemical indices of potential fertility", Int J Gynecol Obstet, 1989, Suppl. 1, pp 35–43.

Collins et al., "Ovarian morphology, endocrine function and intra–follicular blood flow during the peri–ovulatory period", Human Reproduction, 1991, 6(3), pp 319–324.

Collins (1991) Am J Obstet Gynecol, 165(6), p 1994–1996: 'The ecolution of reference methods to monitor ovulation'.

Collins (1992) Biochem Soc Trans, 20, p 234–237: 'Immunochemical tests of potential fertility'.

Colombo (1989) Int J Gynecol Obstet, Suppl 1, p 13–18: 'Biometrical research on some parameters of the menstrual cycle'.

Corsan et al Fertility and Sterility, (1990) 53(4), p 591–601: 'Home urinary luteinizing hormone immunoassays: clinical applications'.

Denari et al (1981) Obstetrics & Gynecology, 58 (1), p 5–9: 'Determination of Ovarian Function Using First Morning Urine Steroid Assays'.

Djerassi (1990) Science, Jun. 1, 1990, p 1061–1062: 'Fertility Awareness: Jet–Age Rhythm Method?'.

Fabres et al (1993) Human Reproduction, 8, p 208–210: 'Validation of the dual analyte assay of the oestrone:pregnanediol ratio in monitoring ovarian function'.

Flynn (1989) Int J Gynecol Obstet, Suppl 1, p 123–127: 'Natural family planning and the new technologies'.

Fordney–Settlage (1981) Int J Fertil, 26, p 161–169: 'A Review of Cervical Mucus and Sperm Interactions in Humans'.

France et al (1975) J Reprod Fert, Suppl 22, p 107–120: 'The Detection of Ovulation in Humans and its Applications in Contraception'.

Garcia et al (1981) Fertility and Sterility, 36(3), p 308–315: 'Prediction of the Time of Ovulation'.

Gudgeon et al (1989) The Medical Journal of Australia, 152, p 344, 346, and 349: 'Evaluation of the accuracy of the home ovulation detection kit, Clearplan, at predicting ovulation'.

Hatcher et al (1994) Contraceptive Technology, 16th Revised Edn. Irvington Publishers, NY, p 327–340: 'Fertility Awareness'.

Ismail et al (1989) Contraception, 39(1), p 53–71: 'An evaluation of the Bioself 110 fertility indicator'.

Judge et al (1978) Steroids, 31(2), p 175–187: 'Time–Course Relationships between Serum LH, Serum Progesterone and Urinary Pregnanediol Concentrations in Normal Women'.

Katz et al (1991) Journal of Andrology, Jan./Feb. 1991, Abstract 29: 'Human Cervical Mucus Properties and Sperm Mucus Interection during the Proliferative Phase of the Menstrual Cycle'.

Katz (1991) Am J Obstet Gynecol, 165(6), Part 2, p 1984–1986: 'Human cervical mucus: Research update'.

Kerin et al (1981) British J obstet Gynecol, 88(2)–90: 'Morphological and Functional Relations of Graafian Follicle Growth to Ovulation in Women Using Ultrasonic, Laparoscopic and Biochemical Measurements'.

Lauzon et al (1992) J Steroid Biochem Molec Biol, 42(2), p 223–228: 'A Direct Dot–Enzyme Immunoassay to Detect Human Ovulation'.

Lewis et al (1993) New Zealand Medical Journal, Apr. 28, 1993, p 165–166: 'Recycling ovulation markers'.

Lewis et al (1994) Steroids, 59, p 288–291: 'Re–examining steroid hormone metabolites as ovulation markers using monoclonal antibodies'.

Landgren et al (1980) *Acta Endocrinologica*, 94, p 89–98: 'Hormonal profile of the cycle in 68 normally menstruating women'.

May (1989) *Proceedings of "Biotec '89" Conference*, Blenheim Online Publications, p 291–295: 'Clearblue One Step: adapting technology to the needs of the consumer'.

Moghissi et al (1972) *Am J Obstet Gynecol*, 114(3), p 405–418: 'A composite picture of the menstrual cycle'.

Moghissi (1980) *Fertility and STerility*, 34(2), p 89–98: 'Prediction and Detection of Ovulation'.

Moghissi (1992) *Reproductive Endocrinology*, 21(1) p 39–55: 'Ovulation Detection'.

Munro et al (1991) *Clin Chem*, 37 (6), p 838–844: 'Relationship of Serum Estradiol and Progesterone Concentrations to the Excretion Profiles of Their Major Urinary Metabolites as Measured by Enzyme Immunoassay and Radioimmunoassay'.

Paz et al (1990) *Gynecol Obstet Invest*, 29, p 207–210: 'Determination of Urinary Luteinizing Hormone for Prediction of Ovulation'.

*Population Reports*, Series 1, No. 3, Sep. 1991, p 1–33—1–71: 'Periodic Abstinence: How well do new approaches work?'.

Royston (1982) *Biometrics*, 38, p 397–406: 'Basal Body Temperature, Ovulation and the Risk of Conception with Special Reference to the Lifetimes of Sperm and Egg'.

Royston (1991) *Statistics in Medicine*, 10, p 221–240: 'Identifying the Fertile Phase of the Human Menstrual Cycle'.

Schiphorst et al (1985) *Fertility and Sterility*, 44(3), p 328–334: 'An estrogen test to determine the times of potential fertility in women'.

Singh et al (1984) *Fertility and Sterility*, 41(2), p 210–217: 'Clinical validation of enzymeimmunoassay of human luteinizing hormone (hLH) in the detection of the preovulatory luteinizing (LH) surge in urine'.

Singh et al (1984) *Hormone Receptors in Growth and Reproduction*, ed Saxena et al, Raven Press, NY, p 341–350: 'Clinical Validation of Enzyme Immunoassay for the Detection of the Preovulatory Luteinizing Hormone Surge in Urine'.

Stanczyk et al (1980) *Am J Obstet Gynecol*, 137(4), p 443–450: 'Direct radioimmunoassay of urinary estrogen and pregnanediol glucuronides during the menstrual cycle'.

*The Economist*, Mar. 23, 1991, p 128–129: 'Fertility: Keeping the beat'.

Tsibris et al (1989) *Int J Gynecol Obstet*, Suppl 1, p 73–82: ' Cervical mucus enzymes as markers of the woman's fertile period'.

Vermesh et al (1987) *Fertility and Sterility*, 47(2), p 259–264: 'Monitoring techniques to—predict and detect ovulation'.

Weerasekera et al (1983) *J Steroid Biochem*, 18(4), p 465–470: 'Multiple Immunoassay: The Simultaneous Measurement of Two Urinary Steroid Glucuronides as an Index of Ovarian Function'.

WHO Task Force (1980) *Am J Obstet Gynecol*, 138(4), p 383–390: 'Temporal relationships between ovulation and defined changes in the concentration of plasma estradiol–17beta, luteinizing hormone, follicle–stimulating hormone, and progesterone'.

WHO Task Force (1981) *Am J Gynecol Obstet*, 139(8), p 886–895: 'Temporal relationships between ovulation and defined changes in the concentration of plasma estradiol–17beta, luteinizing hormone, follicle–stimulating hormone, and progesterone, II. Histologic dating'.

WHO Task Force (1983) *Fertility and Sterility*, 39(5), p 647–655: 'Temporal relationships between indices of the fertile period'.

WHO Task Force (1983) *Fertility and Sterility*, 40 (6), p 773–778: 'A prospective multicentre trial of the ovulation method of natural family planning. III. Characteristics of the menstrual cycle and of the fertile phase'.

WHO Task Force (1985) *Int J Fertil*, 30(3), p 18–30: 'A Prospective Multicentre Study to Develop Universal Immunochemical Tests for Predicting the Fertile Period in Women'.

Wright et al (1979) *Steroids*, 34(4), p 445–457: 'Urinary excretion of estrone glucosiduronate, 17beta–estradiol–17glucosiduronate, and estriol–16alphaglucosiduronate. Significance of proportionate differences during the menstrual cycle. I. Probit analysis'.

Yong et al (1989) *Aust NZ J Obstet Gynecol*, 29, p 155–160: 'Simple Office Methods to Predict Ovulation: The Clinical Usefulness of a New Urine Luteinizing Hormone Kit Compared to Basal Body Temperature, Cervical Mucus and Ultrasound'.

Zinaman et al (1989) *Biology of Reproduction*, 41, p 790–797: 'The Physiology of Sperm Recovered from the Human Cervix: Acrosomal Status and Response to Inducers of the Acrosome Reaction'.

\* cited by examiner

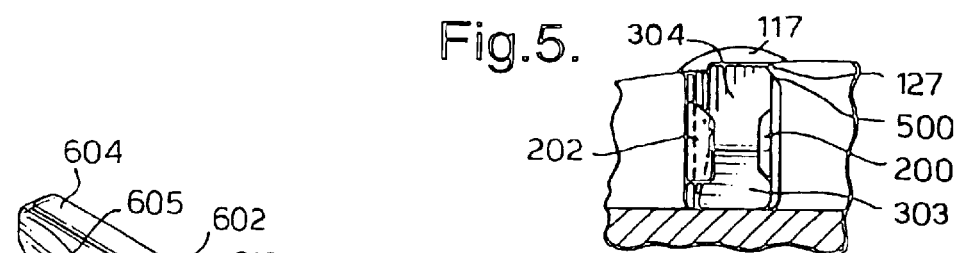
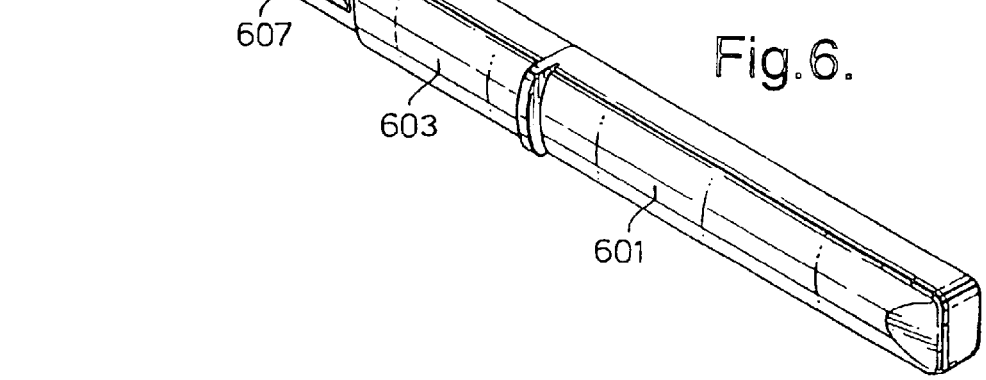
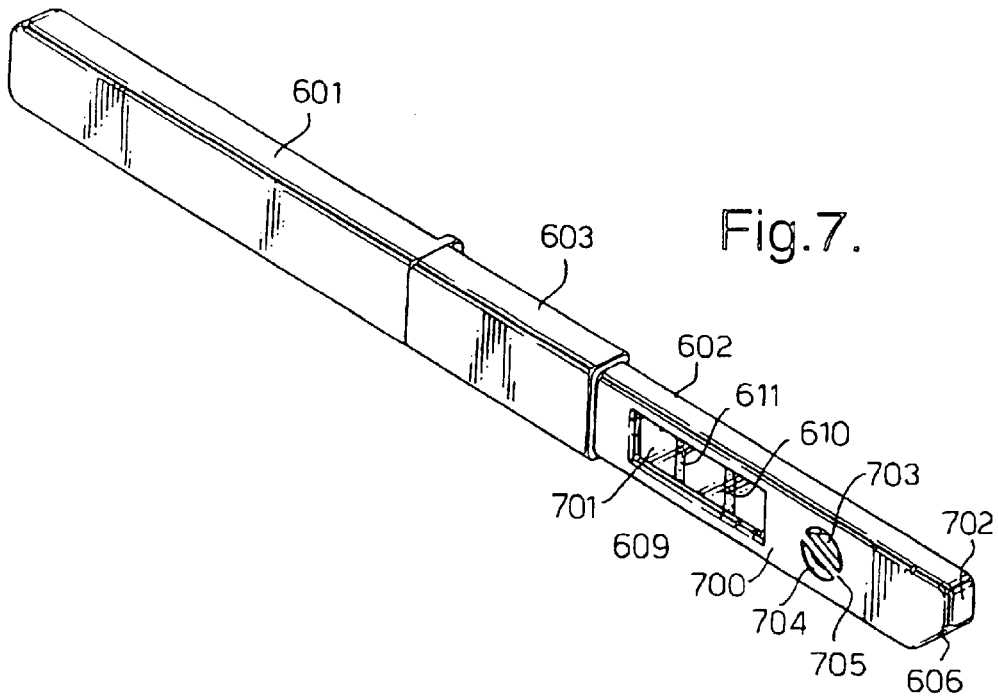

TEST KITS AND DEVICES

FIELD OF THE INVENTION

This invention relates to test kits and devices for determining qualitatively or quantitatively the presence of one or more analytes in a fluid sample, and particularly relates to means to facilitate the correct interaction between an assay device and a reading device therefor which together form essential parts of the test kit.

BACKGROUND TO THE INVENTION

In our PCT patent application WO 95/13531 we describe reading devices for assay devices utilising test strips. Typically the assay device comprises an elongate casing containing the test strip and having in the casing one or more "windows" through which an assay result region or zone of the test strip can be observed. The preferred reading device includes a slotted receiving portion into which the assay device can be inserted and wherein the assay result is determined by electromagnetic means, particularly the transmission of light through the test strip. For accurate determination of the assay result the detection zone of the test strip must be correctly located within the reading device relative to the light path or other features that make up the result reading system. WO 95/13531 describes various ways in which the correct receipt of the assay device within the reading device can be facilitated.

A primary objective of these test kits is that they should be usable by untrained persons and especially by the consumer in the home. When the ordinary consumer is invited to use any apparatus which requires physical engagement of one unit with another, it can be surprisingly common for this action to be performed incorrectly. Carefully worded and illustrated instructions provided by the manufacturer may be mis-interpreted, or often are ignored altogether. In the present context, where the accurate reading of a sensitive assay result is required, it is essential that precise placement of the assay device within the reading device is achieved. Any mis-alignment or incorrect engagement of these two units can lead to an inaccurate or mis-leading assay reading. This problem is particularly acute where the reading system does not include any facility to scan the assay device to locate the appropriate portion that should be read. The cost and complexity of the reading system can be substantially reduced if the precise location of the detection zone within the assay device is controlled during manufacture and the device is presented to the reading device in a constant manner so that the detection zone is always in the same position relative to the reading system. It is an objective of the invention to provide a test kit in which the likelihood of user error during presentation of the assay device to the reading device is substantially reduced. An associated objective is to provide a test kit in which reading of the assay device is not initiated unless the assay device has indeed been correctly presented to the reader, or in which the user is alerted to the mis-presentation of the assay device. In WO 95/13531 we describe some mechanisms to facilitate accurate placement, but the present invention provides further improvements.

The invention will be described with particular reference to test kits useful in monitoring of body fluid analytes, and especially to home monitoring of urinary analytes of relevance to the determination of the status of the human ovulation cycle. This is by way of example only, and it will be appreciated that the invention is useful in many other contexts where other sample liquids and analytes are involved. Examples of other types of analyses, in which accurate assay results are desirable and where a kit in accordance with the invention may be appropriate include assays for cancer markers, cardiac markers, blood glucose, drugs of abuse, hormones, infectious disease markers, tests in therapeutic drug monitoring, manufacturing and raw material quality control, and tests for effluent and pollution levels.

GENERAL DESCRIPTION OF THE INVENTION

The invention provides a test kit for determining qualitatively or quantitatively the presence of one or more analytes in a fluid sample, comprising an assay device together with a reading device which engages with the assay device and wherein precisely located engagement of the assay device with the reading device is essential for accurate reading of the assay result, wherein correct engagement of the assay device with the reading device causes a 'lock-and-key' interaction between the assay device and reading initiation means of the reading device.

In this specification we are using the expression "lock-and-key" interaction to denote a unique 3-dimensional spacial relationship between the assay device and the reading device. In the preferred embodiments of the invention as set out in detail herein this arises through 3-axis alignment of these two components. This 3-axis alignment is translated into a single-axis actuation of a switch means that initiates reading of the assay device.

In one embodiment, the assay device is of the type consisting essentially of a porous carrier strip or the like within a hollow casing and wherein an assay result is revealed by specific binding of a labelled reagent within a detection zone of the carrier strip, the presence of the labelled reagent within the detection zone being discernable by the reading device.

Preferably the reading device includes receiving means for receiving the assay device, and the reading initiation means comprises switch actuating means or the like which is displaceable upon receipt of the assay device within said receiving means, wherein correct receipt of the assay device causes a contact portion of said casing to contact said displaceable switch actuating means, the contact portion and the displaceable switch actuating means being cooperatively engageable via a 'lock-and-key' engagement such that only upon correct receipt of the assay device can the switch actuating means be displaced to initiate reading.

As used herein, the expression "switch actuating means" is used to convey any means that directly or indirectly causes an electrical or electronic circuit to be switched on or off or altered to effect or affect the reading of an assay result. Typically this will be a mechanical mechanism. The actuating means can be part of or directly, e.g. physically, connected to an actual switch, or there can be an indirect or remote connection. The important consideration is that correct engagement of the assay device with the reading device uniquely affects the switch actuating means and, in consequence, the required electrical or electronic change is effected.

Conveniently the switch actuating means comprises at least one fixed projecting portion and at least one displaceable projecting portion, and the contact portion of the assay device casing comprises a recess shaped to accommodate the fixed projecting portion of the switch actuating means but not the displaceable projecting portion thereof, the contact portion also comprising an interface portion that contacts and displaces the displaceable portion of the switch actuating means when the fixed projecting portion is accommodated within the recess.

It is preferred that the receiving means incorporates biasing means that presses the received assay device against the switch actuating means.

In another preferred embodiment, the receiving means incorporates cam means that deflects the assay device away from the switch means unless the assay device is correctly received. Ideally the cam means provides a 'snap' engagement of the assay device and receiving means when the assay device is correctly received.

As a supplementary feature, the assay device is preferably elongate and the receiving means comprises a slot into which at least part of the elongate assay device can fit, and the slot has at least one projecting lip portion extending over the mouth of the slot and which acts to retain the assay device within the slot when correctly received therein. In a preferred version, the projecting lip portion is at one end of the slot and can engage one end of the elongate assay device during insertion of the assay device into the receiving means. Preferably there is also a second projecting lip portion at or near the other end of the slot also to retain the assay device therein.

The invention also extends to any assay device possessing physical features that enable it to engage cooperatively with a reading device in a "lock-and-key" manner as described herein.

A specific embodiment of the invention will now be described in detail with reference to FIGS. 1 to 10 of the accompanying drawings. These drawings are for the purpose of general illustration only, and are not to scale. The reader of this specification should also take note of the technical content of WO 95/13531. The present invention is associated solely with ensuring accurate registration between the assay device and the reading device. The manner in which the assay device generates a readable assay signal is not critical, and neither is the mechanism by which the reading device reads and interprets this signal and provides information to the user. Examples of all these aspects are set out in WO 95/13531.

BRIEF DESCRIPTION OF THE DRAWINGS

FIG. 5 is a partial elevation looking into and along the slot from the right hand end.

FIG. 6 is a general view of an assay device as held by the user in an orientation appropriate for insertion into the reading device.

FIG. 7 is a general view of the opposite side of the assay device.

Referring to FIG. 1, the reading device comprises a generally flattened oval body 100 and a top lid 101 hinged at the rear 102 of the body. Each side 103 of lid 101 curves sharply inwardly adjacent to the hinge, the body 100 is recessed across its upper surface 104 so that when the lid is closed, the device has a flush exterior surface. In this respect the shape and proportions of the lid and body are purely asthetic, and have no bearing on the present invention. There is no technical necessity for the device to have any lid at all. Top surface 104 of the device revealed by the open lid has a recess 105 towards its right hand side 106. Recess 105 has a inwardly sloping rear face 107 which incorporates a number of operating features which are important to the user. These operating features are not of direct relevance to the present invention, but as depicted in FIG. 1 these can include a push-button 108, two indicator lights 109 and 110, and a small display panel 111 to convey information to the user. Recess 105 has a flat floor 112. At the left hand end 113 of recess 105 is an inwardly sloping face 114 from the centre of which a receiving slot 115 extends horizontally towards the left-hand side 116 of the device. Slot 115 extends almost as far as left-hand side of the device, and terminates beneath a small canopy 117 moulded into the upper surface of the device. In FIG. 1 the rear wall 118 of slot 115 can be seen, and features a switch actuating mechanism 119 to initiate reading of an assay device (not shown) when inserted into the slot, and also a rectangular cover 120 of a reading system (hidden within the body of the reading device to obtain information from an inserted assay device. Switch 119 is described below in greater detail with reference to FIGS. 3, 9 and 10. Flat floor 112 of the recess extends into the slot. At the right hand side 121 of recess 105, directly opposite the end 122 of the slot, the rim 123 of the device extends inwardly in a convex curving manner to an apex 124 which is directly in line with the longitudinal axis of the slot. There is a small recess 125 in the inner surface of lid 101 to accommodate canopy 117 at the end of the slot when the lid is closed. Other features of the slot visible in FIG. 1 are that it is substantially parallel-sided throughout most of its length, but a region 126 of the nearer face tapers inwardly slightly as it approaches the canopy. At the other, open, end 122 of the slot there is a forwardly extending lip 127 at the top edge 128 of the rear wall 118. The slot is widest at its open end 122, because both the front wall and the rear wall are stepped outwardly in regions 129 and 130 respectively.

Referring to FIG. 2, these same features of slot 115 can be seen more clearly. Additional features visible in FIG. 2 are that the rectangular cover 120 for the reading system extends outwardly from the rear wall 118 of slot 115 and has sharply bevelled edges 200. In the forward wall 126 of the slot are two projecting spring-loaded buttons 201 and 202, one (201) being directly opposite the actuating switch 119 and the other (202) being near the mouth 122 of the slot, opposite the lip 127 that extends from the rear wall 118. Second button 202 has a bevelled face 203 adjacent the mouth of the slot.

FIG. 3 shows the rear wall 118 of slot 115. The switch actuator 119 is divided into three components. The overall form is circular, but it comprises a diagonal central portion 300 extending across the entire width of the actuator, and two arcuate portions, 301 and 302, one on each side of the diagonal. The arcuate portions are fixed, but the central diagonal portion is depressable inwardly to actuate reading by the device. FIG. 3 also shows that a region 303 of the flat floor 131 of the slot, adjacent canopy 117, slopes upward sharply to meet the end wall 304 of the slot beneath the canopy.

FIG. 4 shows the opposite wall 126 of slot 115, including the two spring-loaded buttons 201 and 202. The button 202 adjacent the mouth 122 of the slot is of asymmetric shape and its top 400 is bevelled downwardly and the left hand face 203 (as seen in FIG. 4) is also bevelled. Situated horizontally between the two buttons is a rectangular recess 401 behind which is an illuminating system (not seen) which forms part of the assay reading mechanism. Recess 401 is situated directly opposite the protruding cover 120 of the reading system in the opposite wall of the slot. Again, the upwardly sloping region 303 of floor 131 of the slot can be seen beneath canopy 117.

Figure 1:
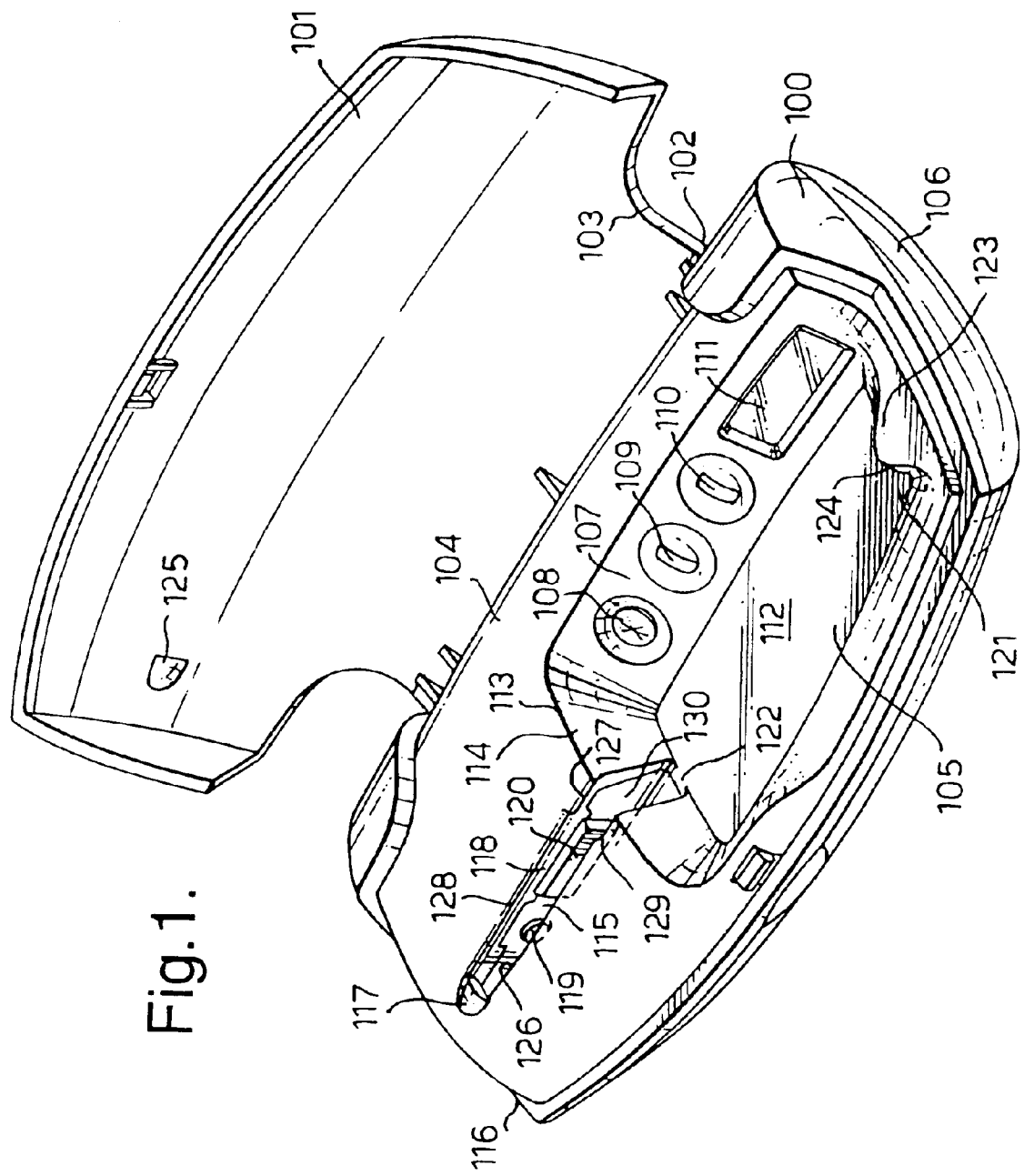
FIG. 1 represents a general view of a reading device of the invention, with an open lid revealing the main user-related features of the device.
Figure 2:
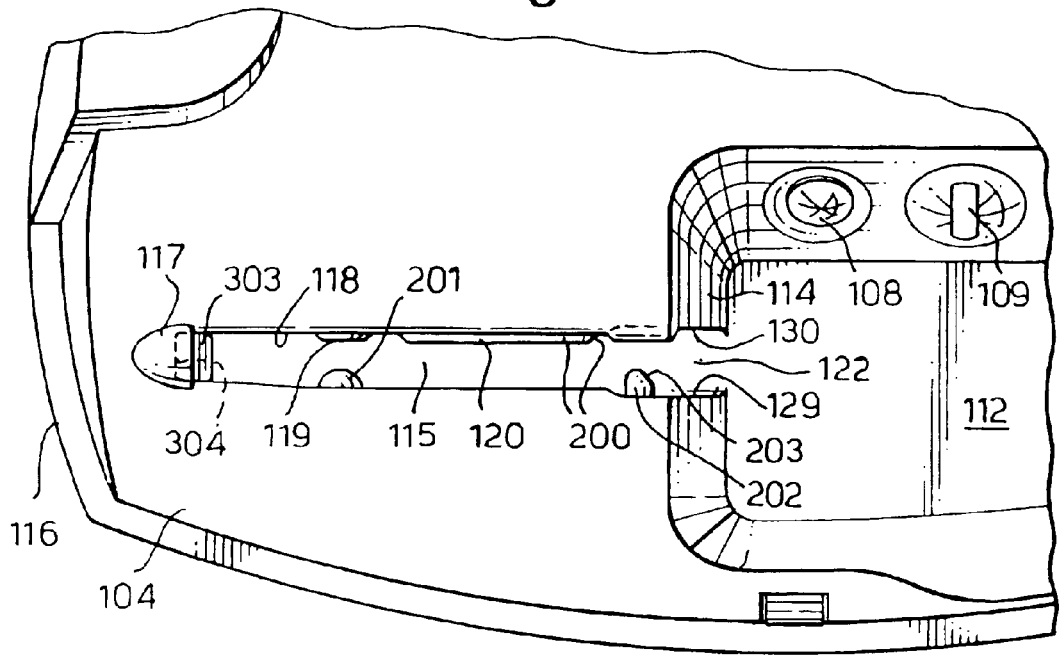
FIG. 2 represents a plan view of part of the device seen in FIG. 1, showing in detail a slot for receiving an assay device.
Figure 3:
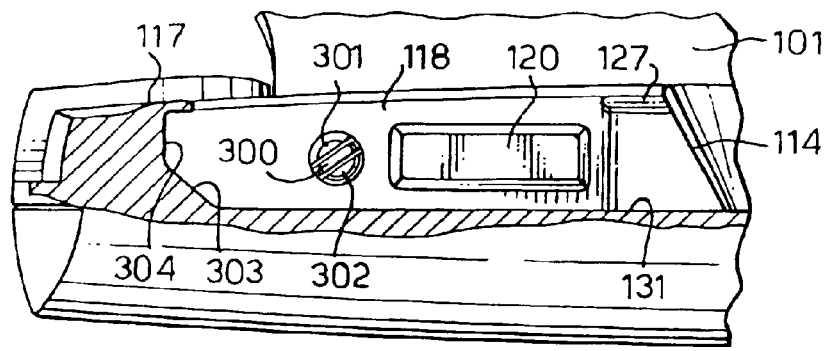
FIG. 3 is a partial cross-section of the reading device, taken on the longitudinal axis of the slot, showing the rear wall of the slot.
Figure 4:
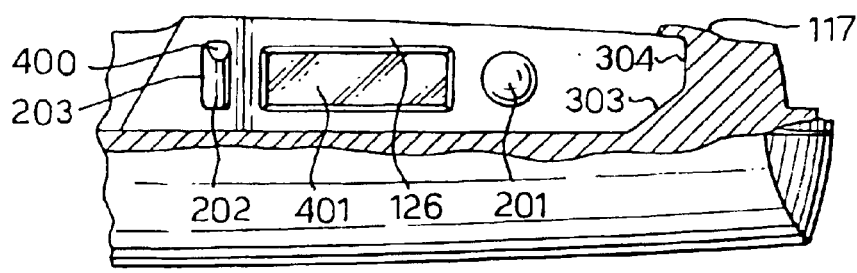
FIG. 4 is a partial cross-section of the reading device, again taken on the longitudinal axis of the slot but viewed in the reverse direction, showing the opposite wall of the slot.

The view along slot 115 as seen in FIG. 5 shows that the underside 500 of projecting lip has a convex curved surface. Other features seen in FIG. 5 are the bevelled pressure button 202, the protruding reading system cover 120, the canopy 117 at the far end of the slot, and the upwardly sloping floor 303 beneath the canopy.

FIG. 6 shows an assay device comprising an elongate body 600 and a removeable cap 601. The left hand portion 602 (as seen in FIG. 6) of body 600 is of narrower cross-section than the main portion 603 and tapers sharply at its extreme left hand end 604. This tapering results from:
a) Front face 605 of the device being bevelled towards the left hand end; and
b) Lower surface 606 being angled sharply upwards at the left hand end.

There is a long rectangular window 607 in the front face 605 of the narrower portion 602 of the body, having angled sides 608 extending into the body moulding. This window reveals an assay strip 609 within the device and, as shown, this includes two assay result zones 610 and 611.

Referring to FIG. 7, which shows the opposite side of the assay device, the opposing face 700 of the narrower portion 602 of the body also incorporates a rectangular window 701 recessed into the body. This window reveals also the strip 609 and the same detection zones 610 and 611, as seen through the other window. In this same face of the device, between window 701 and the extreme tip 702 are a pair of arcuate recesses 703 and 704 separated by a diagonal portion 705 which is flush with the remainder of the device surface at this point.

Figure 8:
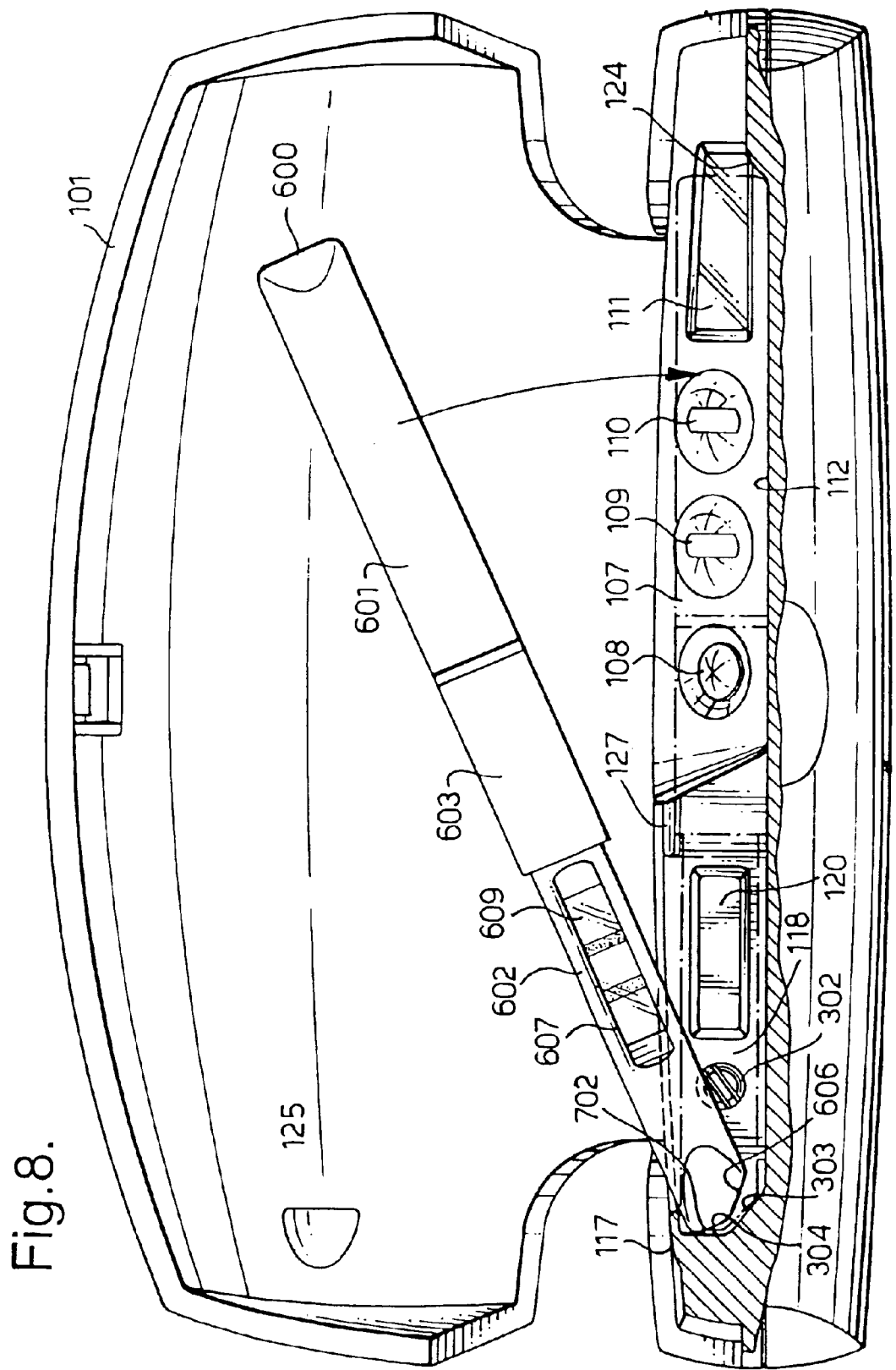
FIG. 8 is a partial cross-sectional elevation of the reading device and assay device during insertion, viewed from the front of the reading device.

FIG. 8 shows the assay device 600 being inserted into the reading device. The tip 702 of the assay device body has been placed beneath canopy 117 and, at about the mid-point of the narrower portion 602 of the body, it is contacting and resting the upper part of pressure button 201, although this is not seen in this drawing. This is a stable position, and it requires finger pressure by the user downwardly on the body 603 and/or cap 601 of the device to push the device into a more horizontal orientation within the slot, against the resistance created by pressure button 201 which would be displaced by such motion. This drawing also shows, in broken lines, the position that the assay device needs to occupy when correctly inserted in the reading device for accurate reading. This correct position requires the assay device to be fully horizontal (relative to the reading device floor) with tip 702 fully home under canopy 117 and the far end 800 of the cap abutting the inwardly curving portion 124 of the right hand side of the reading device. It can also be seen that the upwardly sloping portion 606 of the tip 702 of the assay device matches the upward slope 303 of the floor of the slot beneath the canopy. When the assay device is correctly inserted in the slot, the broader portion 603 of the body is retained snuggly beneath the projections lip 127 of the rear wall 118 of the slot.

Figure 9:
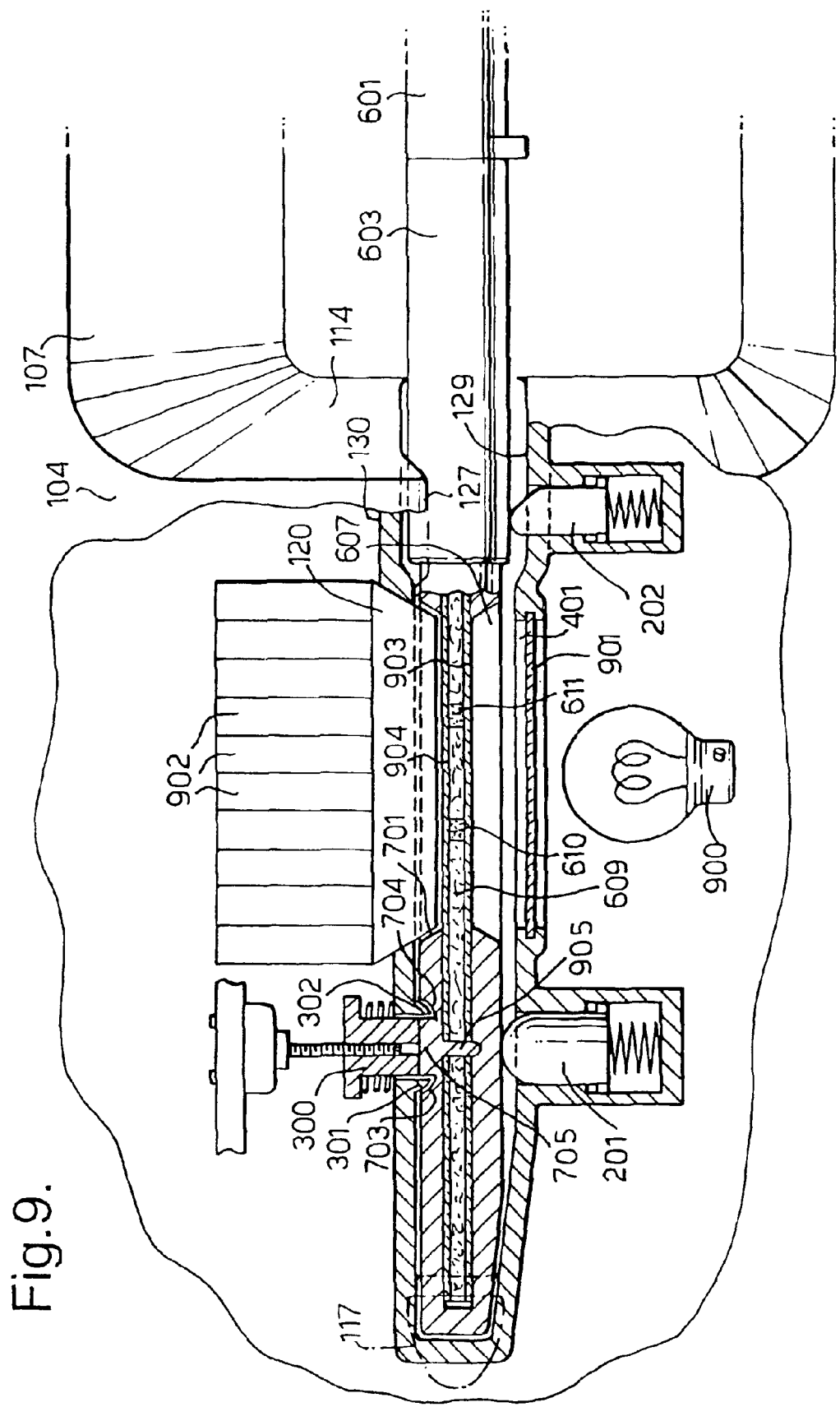
FIG. 9 is a plan view, partially cross-sectional and partially cut away, of the slot with the assay device correctly inserted therein.

Referring to FIG. 9, the correctly inserted assay device is locked in place by a combination of features. It is urged against the rear wall 118 of the slot by pressure from the two pressure buttons 201 and 202. The protruding cover 120 of the reading system fits precisely into the window recess 701 in the assay device body. The fixed arcuate portions 301 and 302 of switch actuator fit precisely into the arcuate recesses 703 and 704 in the assay device body, and the central diagonal portion 300 of the switch is depressed by the diagonal body portion 705 between the two recesses. Depression of the portion 300 of the switch actuator causes reading of the assay device by a mechanism described below with reference to FIG. 10. The objective is to provide a unique three-dimensional situation in which the switch actuator is actuated by the received assay device. The positions of the canopy 117 and the protruding lip 127 are shown in broken lines. The broader portion 603 of the body of the assay device is accommodated within the outwardly flared mouth of the slot.

Other features shown in FIG. 9 are an illumination system 900 behind an optical diffuser 901 in the forward wall 126 of the slot, and a series of optical sensors 902 behind the cover 120 on the rear wall 118 of the slot. These features are simply represented diagrammatically as they are not critical to the present invention. Appropriate examples of such features are described in WO 95/13531.

Features seen within the partial cross-section of the assay device are the assay strip 609 sandwiched on each side by a transparent plastics sheet 903 and 904, the two detection zones 610 and 611 in the strip, and a pin 905 in the assay device moulding which extends through the assay strip and covering sheets to provide during manufacture of the device a precise location means for the two detection zones. Examples of these features are also fully described in WO 95/13531.

Figure 10:
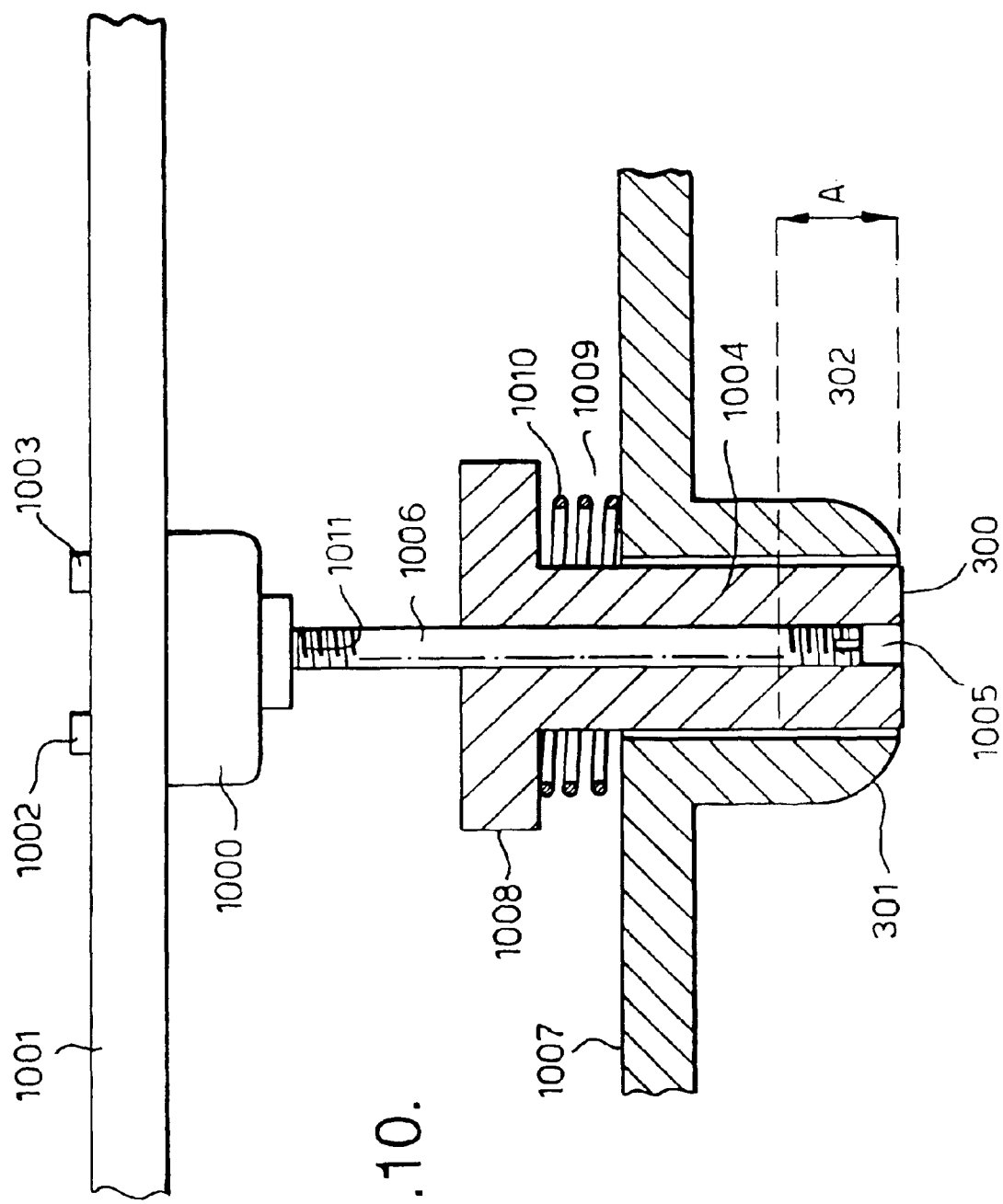
FIG. 10 is an enlarged plan view, in partial cross-section, of the switch actuating mechanism of the reading device.

FIG. 10 shows the switch actuating mechanism of the reading device in greater detail. The actual switch 1000 which is connected to the electronic processor within the reading device is itself within the interior of device, body 100 and in the preceding drawings is only visible in the partly cut-away FIG. 9. The actual unit 119 which is visible on the rear face of slot is a separate mechanical construction which makes contact with and operates switch 1000 during use. As depicted in FIG. 10, switch 1000 is situated on a printed circuit board 1001. At the rear of circuit board 1001 are two switch contacts 1002 and 1003.

The mechanical construction which interacts with a correctly inserted testing device is located in the rear wall of slot. As already described, the mechanism comprises two outer fixed portions 301 and 302, and a central movable portion 300 which is displaced inwardly when the testing device is correctly inserted. As depicted in FIG. 10, the movable portion 300 of the actuating mechanism comprises a hollow shaft 1004 which rests between the two fixed portions of the mechanism, and forms a freely-sliding bearing between 301 and 302. A threaded passageway 1005 extends axially through the entire shaft and engages with a long threaded screw 1006 held within the shaft. The shaft extends beyond the inner face 1007 of the slot wall and terminates in a flange 1008. The width of flanged portion of the shaft exceeds the width of the channel between the two fixed portions of the mechanism which accommodate the bulk of the spine. A gap 1009 exists between the flange and the wall of the slot, and within this gap is a helical spring

1010, the ends of which abut the flange and the inner wall surface. Spring 1010 acts to lightly bias the position of the shaft soo that the end 1011 of the screw abuts the switch when the mechanism is in its rest position, which is as shown in FIG. 10. The force of spring 1010 is less than the force required to actuate the switch. Threaded screw 1006 extends beyond flange 1008.

During manufacture of the reading device, screw 1006 can be adjusted so that the outer surface of central shaft 300 is at a distance A displaced from the tips of fixed portions 301 and 302 when contact is established within the switch. Control of this manufacturing adjustment can be achieved by sensing the switch contacts.

During the recommended mode of insertion of the assay device into the reading device, as generally illustrated in FIG. 8, the "toe" of the assay device is placed beneath the canopy 117 and finger pressure forces the assay device downwardly, pivoting against the fulcrum created by the lip of the canopy, and "snapped" past the various features which protrude from either wall into the void of the slot. The protruding cover 120, and to a lesser extent the fixed portions of the actuating switch and protruding lip 127, act as cams which force the body of the device away from the rear wall and against the two pressure buttons. As the assay device is rotated downwardly and the protruding cover and fixed portions of the actuating switch begin to engage with their appropriate recesses in the assay device body, the pressure created by the pressure buttons forces the assay device towards the rear wall of the slot and it can "snap" into position beneath the protruding lip. The curvature of the underside of the protruding lip facilitates this final motion of the assay device into its appropriate reading location. If the assay device is moulded from plastics material, such as polystyrene, as is conventional today in mass-produced diagnostic devices, it can have sufficient flexibility to distort and facilitate this motion. Indeed, the natural resilience of the assay device moulding can be exploited to advantage, because the deformation and subsequent release when the assay device is correctly received within the reading device can enhance the "snap" engagement between these two kit components. The edges of the assay device moulding, and of the points of contact on the reading device, can be radiused to facilitate sliding motion between these components, and to avoid situations in which the two components might jam together.

It is also possible for the user to insert the assay device into the slot to reach its correct reading position by placing the tip of the device in the open end of the slot and pushing the device horizontally until it is fully home in the slot. At the conclusion of this alternative procedure the assay device will again be held precisely in place by the various interactions described above.

If for any reason the assay device is incorrectly inserted into the slot during normal use, the precise registration of these various features will not be realised. The actuating switch will not be depressed. If desired, a supplementary sensing mechanism can be incorporated to detect the presence of an incorrectly inserted assay device so that a warning signal may be conveyed to the user that the assay device is not in its correct location.

The body of the reading device, including the walls and floor of the slot, can be moulded from durable plastics material, such as polystyrene. The pressure buttons, and the projecting portions of the switch-actuating mechanism are preferably made from more robust material, because these must withstand repeated contact with the disposable testing devices over an extended period of use. So-called "hard engineering plastic", such as ABS, is ideal. This has good dimensional stability and is harder than polystyrene. The material should have natural bearing properties. An ideal commercially available ABS is "Delrin".

The precise form and relationship of the various features described above, which provide a positive three-dimensional interlock when the assay device is correctly inserted, are for the purpose of example only. The skilled reader will readily appreciate that a wide variety of alternative profiles and constructions can be used to achieve a functionally comparable positive interlocking action.

By way of background and example, the invention facilitates the provision of assay result reading devices and associated sample testing devices which can provide accurate quantitative assay information in a simple, quick and cost effective manner. Such devices can be used in a wide range of situations such as hospitals, clinics, doctors' offices, and the home. Depending on the circumstances, the analyte under investigation can also vary widely. Examples are infectious disease organisms or markers, metabolites in body fluids indicative of a change in the health or condition of a patient, and administrable or ingestable substances such as medicaments or drugs of abuse. Assay formats are required which can be performed by comparatively untrained people and especially in the home. Home-use assays are intended primarily to detect physiological changes in the human body, with the objective of promoting the health, general well-being or lifestyle of the individual. The consumer is becoming increasingly health conscious, and the ability of the consumer to monitor his or her bodily functions is being encouraged. In some instances this can facilitate the interaction between the individual consumer and the medical profession (GP).

There are many assays indicative of physiological changes in the human body which currently can only be performed using sophisticated laboratory techniques. In order to provide useful information concerning the individual under test, such assays generally need to yield a result in precise numerical terms, eg. the concentration of a specific analyte in a body fluid. Accordingly there is a need for improved assay systems, especially applicable to the testing of body fluid samples in the home, which combine convenience of sample testing together with simple and cost-effective numerical determination of the assay result.

Many assay devices are described in the technical literature with suggestions that the assay result can be read using optical equipment. The use of fluorescence emission, or light reflectance, is often suggested. Such techniques are mostly appropriate for use in sophisticated laboratories, although optical reflectance is used in commercially-available blood glucose tests. In WO 95/13531 we describe reading systems using optical transmission through an assay strip or similar membrane.

The assay device/reader combination can be supplied to the consumer as a single test kit. In general however, whereas the reader will be a relatively permanent unit which the consumer can use time and again (and which may be provided with an electronic memory/data-processing facility which enables the results of many sequential assays to be evaluated) the testing devices will be intended for use only once and thereafter will be discarded. Accordingly, the test devices may be supplied to the consumer separately from the reader, e.g. in multi-packs.

By ensuring precise interlocking between the testing device and the reader, and also ensuring precise registration of the location of the detection zone within the testing device itself, the testing zone will be presented to the reader in a constant pre-determined position every time a testing device is inserted into the reader. The construction of the optical system within the reader (light source and sensors) can therefore be kept as simple as possible, because it is not essential for the sensors to include any scanning facility, for example, which would otherwise be required if the exact location of the detection zone was not known. By avoiding the need for a sophisticated optical reading system, the cost of the reader/monitor may be reduced. Simplification of the optical reading system may also enable the reader/monitor to be of small size which will assist convenient and unobtrusive use in the home. Of course, a scanning facility can be included in the reader if desired.

An additional benefit of providing an internal registration system which ensures precise location of the detection zone within the test device, is that automated manufacture and quality control of the testing devices can be facilitated. Because it is envisaged, for example, in the case of an ovulation cycle monitor, that the consumer will need to use several testing devices each month, the testing devices may need to be manufactured in large numbers at low cost. Internal registration can facilitate automated manufacture and high throughput.

In principle, any electromagnetic radiation can be used to effect a transmission measurement. The electromagnetic radiation should preferably be capable of being rendered diffuse. Preferably the electromagnetic radiation is light in the visible or near-visible range. This includes infra-red light and ultra-violet light. It is generally envisaged that the detectable material used as a label in the assay is one which will interact with light in the visible or near visible range, eg. by absorption. The wavelength of the electromagnetic radiation chosen is preferably at or near a wavelength which is strongly influenced, eg. absorbed, by the label. For example, if the label is a substance which is strongly coloured, ie. visible to the naked human eye when the material is concentrated, the ideal electromagnetic radiation is light of a complementary wavelength. Particulate direct labels, for example, metallic (eg. gold) sols, non-metallic elemental (e.g. Selenium, carbon) sols, dye sols and coloured latex (polystyrene) particles are ideal examples. For instance, in the case of blue-dyed latex particles, the ideal electromagnetic radiaation is visible red light which will be strongly absorbed by the blue particles.

A primary advantage of the use of diffuse light or other radiation in this context is that the reading of the assay result is much less likely to be adversely influenced by blemishes or contaminating material on the assay device For example, dirt or scratches on the assay device in the region through which the radiation must be transmitted could strongly interfere with the accuracy of the determined result if focussed rather than diffuse light is used. By the use of a diffuse light source, it is possible to provide an assay result reader which can accurately interpret the result of an assay conducted even in an essentially transparent assay device without the assay result being adversely affected by minor contamination or damage (eg. superficial scratches) to the assay device.

Desirably, the electromagnetic radiation from the source is pulsed. By synchronising the detectors (sensors) so that they function only in phase with the pulsed radiation source, it is possible to eliminate any background interference that might be caused by external radiation, e.g. ambient light. Home-use assays will mostly be conducted under circumstances of natural daylight or, even more often, artificial light. Artificial light is usually of a pulsed nature (typically 50–100 Hz) caused by the alternating nature of electricity supplies. By adopting a pulsed radiation source for the illumination of the assay device within the reader, the intrusion of natural daylight can be ignored. By selecting the pulse frequency such that it is sufficiently different from the prevailing artificial light, any interference due to artificial light can also be avoided. Preferably the pulse frequency of the energy should be at least about 1 kHz. An ideal pulse frequency is about 16 kHz. The electronics necessary to achieve synchronous pulsed sensing are familiar to those skilled in the art. The use of pulsed light is very advantageous because it renders it unnecessary for the monitor to be "light tight". Not merely does this simplify the construction of the monitor but the reading of the assay result can be performed while the monitor is "open", thus simplifying the operation for the user.

The source of light or other electromagnetic radiation can comprise entirely conventional components. Ideal examples are commercially available LED's, preferably chosen to give a suitable wavelength of light that is strongly absorbed by the detectable material concentrated in the test zone(s). Light from the LED's should be passed through a strong diffuser before reaching the assay device. If desired, an array of LED's which are energised in turn can be used.

Suitable diffusers can be made, for example, from plastics materials, and are available commercially. If necessary, the light-scattering properties of the diffusing material can be enhanced by including particulate materials such as Titanium dioxide and Barium sulphate. An ideal diffusing material comprises polyester or polycarbonate, containing Titanium dioxide. A good inclusion level for the particulate material is at least about 1% by weight, preferably about 2%. By the use of a diffuser, all relevant regions of an assay strip may be measured simultaneously, and differences in light output from the source are eliminated.

The sensor(s) to detect emergent light can be conventional components such as photodiodes, e.g. silicon photodiodes.

Preferably, a second diffuser, which can be made from the same material as the primary diffuser, is located in front of the sensor(s). This ensures that the view seen by the sensor is not affected by the presence or absence of a test strip in the reading head. In consequence, the monitor can be calibrated in the absence of a test strip, and then measure an assay result in the presence of an assay strip.

By employing a uniform light source it is possible to provide a reading system for test strips and the like which is relatively tolerant to variation in the placement of the test zone(s) from one strip to another, in the absence of a scanning sensor. However, very substantial benefits in terms of assay accuracy are obtained if test zone placement is controlled, as described herein.

For the purposes of enhancing the likelihood of conception, assay devices have already been marketed which enable the user to monitor the urinary concentration of lutenizing hormone (LH) which peaks sharply approximately one day in advance of ovulation. Daily testing of urinary LH concentration is conducted, for example using "dipstick" technology with the assay result being provided by a coloured end point, the intensity of the colour being proportional to LH concentration. By providing the consumer with a colour chart which enables the daily result to be compared against a standard, the "LH surge" can be detected simply by eye. Unfortunately, the monitoring of LH concentration is a very rare example of an assay relying on semi-quantitative data which is ameniable to such simple technology, being possible only because in relative concentration terms the LH surge is such a dramatic event. For most other potentially useful assays the analyte concentration changes in body fluids are much more subtle and only detectable accurately by instrumental means.

A need therefore exists to extend the currently available qualitative home-use testing technology into the area of precise quantitative testing. A convenient example, which is a logical extension of the present consumer interest in home-use pregnancy testing and ovulation prediction testing, is the extension into accurate monitoring of the ovulation cycle, not merely to enhance the likelihood of conception but indeed to provide reliable information for the purposes of contraception. Proposals have been made to analyse body fluids with this objective in mind. A common theme is to monitor periodic fluctuations in various hormone metabolite levels in urine.

The improved test kits of the invention can be used in the determination of any body fluid analyte, especially in the monitoring of the human ovulation cycle by the determination of one or more hormones or metabolites thereof in body fluid, such as urine, for example either LH and/or estrone-3-glucuronide (E3G). The last few decades have seen much research conducted into ways of enhancing "natural" family planning, in which physiological parameters indicative of the status of the ovulation cycle are monitored. In EP-A-706346 we particularly describe such a method which uses the measurement of urinary estradiol or metabolites thereof, especially estrone-3-glucuronide (E3G), to provide a warning of the onset of the fertile phase. Related methods are described in EP-A-656118, EP-A-656119 and EP-A-656120. Associated testing devices and test kits are described in these specifications, and also in WO 96/09553.

Within this context it is envisaged that a home-use sample liquid testing device will generally include a porous carrier material, such as a strip, through which applied sample liquid such as urine can permeate and wherein the assay result occurs by means of specific binding of a detectable material in a precisely-defined region (detection zone) of the carrier, such as a narrow line or small dot, containing an immobilized specific binding reagent. The invention is therefore concerned with ways in which localisation of a detectable material in such a detection zone can be determined accurately in a simple and cost-effective manner. Home-use devices for the analysis of urine, for example in pregnancy tests and ovulation prediction tests, are now widely available commercially. Many such devices are based on the principles of immunochromatography, and typically comprise a hollow casing constructed of plastics material containing a porous assay strip carrying pre-dosed reagents. The reagents within the device may include one or more reagents labelled with a direct label, such as a dye sol, a metallic (e.g. gold) sol, or a coloured latex (e.g. polystyrene) microparticle, which are visible to the eye when concentrated in a comparatively small test area of the strip. The user merely needs to apply a urine sample to one part of the casing to initiate the assay. The assay result becomes visible by eye within a few minutes without further action by the user. Examples of such devices are described in EP-A-291194 and EP-A-383619. Sample collection is conveniently achieved by means of a bibulous member which forms part of the device and which can readily take up sample liquid, e.g. from a urine stream. Optionally the bibulous member can protrude from the casing of the device to facilitate sample application. In addition to the specific examples of detectable materials already mentioned above, other materials can be used which block or reflect the electromagnetic radiation, rather than absorb it, e.g. "white" particles such as latex particles in their natural uncoloured state. Alternatively, the label can be a reactant or catalyst which participates in the generation of a radiation absorbing or radiation-blocking material, e.g. an enzyme which reacts with a substrate to produce a detectable material, such as a coloured material, in the detection zone.

It is generally envisaged that the material of the casing will be opaque, e.g. white or coloured plastics material, but the casing can be translucent or indeed transparent if desired.

The iluminator can consist of a series of LEDs embedded in or placed behind a diffusing medium which provides a uniform and diffuse illumination of the test strip covering the reference and signal zones.

The incorporation of a diffuser between the apertures and the test strip is beneficial for calibration purposes. In order to calibrate each of the optical channels in the absence of the test strip it is highly desirable that each detector is collecting light from the same areas of the illuminator as is the case when a test device is present. The diffuser can be selected to be the dominant diffuser in the optical path so that the introduction of the test strip does not contribute signifiantly to changes in the illumination distribution observed by the detectors. In addition, the diffuser element can enable the optical assembly to incorporate a 'wipe clean' surface, desirable for long-term repeated performance of the optical assembly. By modulating the intensity of the illuminator, the optical channels can be calibrated, without the aid of moveable parts, 'invisibly' to the user prior to the insertion of a test device.

The test strip can consist of an optically diffuse layer of nitrocellulose or the like, preferably sandwiched between two layers of optically clear film, e.g. of polyester such as "Mylar". The clear film protects the nitrocelluose within which the assay reactions take place. Making reflectance measurements through thin transparent films is particularly difficult because of problems arising from specular reflections. Transmission measurement allows the optics to be constructed orthogonal to the measuring suface and minimises the adverse effects of reflection.

The invention is particularly applicable to the reading of test strips made of nitrocellulose and similar diffuse membranes that preferably do not exceed about 1 mm thickness.

The constituent parts of the casing can be moulded from high impact or similar plastics materials such as polystyrene and polycarbonate and held together by "push fit" clips or threaded screws or any other appropriate mechanism.

It will be appreciated that the overall layout and general shape of the monitor can be subject to very considerable variation from that described above without departing from the scope of the invention. The general shape and layout of the reading head is dictated by the need to cooperate effectively with the assay device but this shape can be varied considerably. The layout and nature of the user accessible controls and information display features can likewise be subject to considerable variation and are dictated to a large extent by aesthetic considerations.

The detailed electronics of a monitoring device capable of assimilating, remembering and handling analyte concentration data, as well as providing the preferred electronic features of the device discussed herein, and where appropriate predicting future events, such as the fertility status in an ovulation cycle on the basis of such data, can readily be provided by those skilled in the electronics art once they have been advised of the factors that such a device must take into consideration, and the information that the device must provide for the user. The individual features can be entirely conventional, and those familiar with the art of electronics will appreciate that other combinations and arrangements of such features can be employed to achieve the objectives of the invention. For example, so-called "hard-wired" systems, and "neural networks", can be used in place of conventional microprocessors based on "chip" technology.

Information can be conveyed to the user by means of a liquid crystal or LED display, for example. If desired, information on the state of fertility can be conveyed by a simple visual indication, eg a combination of colours showing, for example, green for infertile and red for fertile. Especially if the device is intended primarily as an aid to contraception, it should "fail safe" by showing a "fertile" signal.

What is claimed is:

1. A test kit for determining qualitatively or quantitatively the presence of an analyte in a fluid sample, said test kit comprising;
    an assay device, said assay device having a detection zone, wherein the presence of the analyte in the fluid sample is indicated by accumulation of a labeled reagent within the detection zone; and
    (b) a reading device effective to detect labeled reagent, said reading device comprising means for initiation of the reading device to detect labeled reagent in the detection zone,
wherein the means for initiation of said reading device comprises a switch actuator, and wherein said assay device comprises a contact portion, said contact portion and said switch actuator engaging in a lock-and-key engagement,
wherein the reading device further comprises means for pressing an assay device inserted into the reading device against the switch actuator,
wherein the reading device further comprises a cam that deflects the assay device away from the switch actuator unless the assay device is correctly positioned within the reading device,
wherein the assay device is elongate, and wherein the reading device has a slot into which the assay device is at least partially inserted through a mouth for reading of the assay device, and wherein the slot has at least one projecting lip portion extending over the mouth of the slot, said lip portion acting to retain the assay device within the slot when correctly positioned therein,
wherein said means for initiation of the reading device engages the assay device in a lock-and-key interaction, thereby forming a lock-and-key interaction between the reading device and the assay device whereby the reading device is initiated in response to and only when said assay device is properly positioned in lock-and-key engagement within said reading device and the lock-and-key interaction is formed.

2. The test kit of claim 1, wherein said assay device comprises a porous carrier strip disposed within a hollow casing, said porous carrier strip having the detection zone, and wherein an assay result is revealed by specific binding of the labeled reagent within the detection zone.

3. The test kit of claim 2, wherein the switch actuator comprises a fixed projecting portion and a displaceable projecting portion, and wherein the contact portion has
    a recess for receiving the fixed projecting portion, but not the displaceable projecting portion, when the assay device is correctly positioned in the reading device; and
    an interface portion that contacts and displaces the displaceable projecting portion when the assay device is correctly positioned in the reading device.

4. The test kit of claim 2, wherein the projecting lip portion is disposed at an end of the slot, and engages an end of the elongate assay device during insertion of the assay device into the slot.

5. The test kit of claim 1, wherein the projecting lip portion is disposed at an end of the slot, and engages an end of the elongate assay device during insertion of the assay device into the slot.

6. A test kit for determining qualitatively or quantitatively the presence of an analyte in a fluid sample, said test kit comprising;
    an assay device, said assay device having a detection zone, wherein the presence of the analyte in the fluid sample is indicated by accumulation of a labeled reagent within the detection zone; and
    (b) a reading device effective to detect labeled reagent, said reading device comprising means for initiation of the reading device to detect labeled reagent in the detection zone,
wherein the means for initiation of said reading device comprises a switch actuator, and wherein said assay device comprises a contact portion, said contact portion and said switch actuator engaging in a lock-and-key engagement,
wherein the switch actuator comprises a fixed projecting portion and a displaceable projecting portion, and wherein the contact portion has
    a recess for receiving the fixed projecting portion, but not the displaceable projecting portion, when the assay device is correctly positioned in the reading device; and
    an interface portion that contacts and displaces the displaceable projecting portion when the assay device is correctly positioned in the reading device,
wherein the reading device further comprises means for pressing an assay device inserted into the reading device against the switch actuator,
wherein the reading device further comprises a cam that deflects the assay device away from the switch actuator unless the assay device is correctly positioned within the reading device,
wherein the assay device is elongate, and wherein the reading device has a slot into which the assay device is at least partially inserted through a mouth for reading of the assay device, and wherein the slot has at least one projecting lip portion extending over the mouth of the slot, said lip portion acting to retain the assay device within the slot when correctly positioned therein,
wherein said means for initiation of the reading device engages the assay device in a lock-and-key interaction, thereby forming a lock-and-key interaction between the reading device and the assay device whereby the reading device is initiated in response to and only when said assay device is properly positioned in lock-and-key engagement within said reading device and the lock-and-key interaction is formed.

7. The test kit of claim 6, wherein the projecting lip portion is disposed at an end of the slot, and engages an end of the elongate assay device during insertion of the assay device into the slot.

8. A test kit for determining qualitatively or quantitatively the presence of an analyte in a fluid sample, said test kit comprising:
    (a) an assay device, said assay device having a detection zone, wherein the presence of the analyte in the fluid sample is indicated by accumulation of a labeled reagent within the detection zone; and
    (b) a reading device effective to detect labeled reagent, said reading device comprising means for initiation of the reading device to detect labeled reagent in the detection zone,
wherein said means for initiation of the reading device engages the assay device in a lock-and-key interaction, whereby the reading device is initiated in response to and only when said assay device is properly positioned in lock-and-key engagement within said reading device, wherein the assay device is elongate, and wherein the reading device has a slot into which the assay device is at least partially inserted through a mouth for reading of the assay device, and wherein the slot has at least one projecting lip portion extending over the mouth of the slot, said lip portion acting to retain the assay device within the slot when correctly positioned therein.

* * * * *